United States Patent
White et al.

(10) Patent No.: US 7,862,618 B2
(45) Date of Patent: Jan. 4, 2011

(54) EXPANDABLE VERTEBRAL BODY IMPLANTS AND METHODS OF USE

(75) Inventors: John White, Bartlett, TN (US); Jason A. Edie, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 810 days.

(21) Appl. No.: 11/489,189

(22) Filed: Jul. 19, 2006

(65) Prior Publication Data

US 2008/0021555 A1 Jan. 24, 2008

(51) Int. Cl.
*A61F 2/44* (2006.01)
(52) U.S. Cl. .................... 623/17.16; 623/17.11
(58) Field of Classification Search ... 623/17.11–17.16; 606/246
See application file for complete search history.

(56) References Cited

U.S. PATENT DOCUMENTS

| | | | |
|---|---|---|---|
| 4,401,112 A | 8/1983 | Rezaian | |
| 4,553,273 A * | 11/1985 | Wu | 623/23.45 |
| 4,554,914 A | 11/1985 | Kapp et al. | |
| 4,599,086 A | 7/1986 | Doty | |
| 4,636,217 A | 1/1987 | Ogilvie et al. | |
| 4,657,550 A * | 4/1987 | Daher | 623/17.11 |
| 4,737,394 A | 4/1988 | Zafiroglu | |
| 4,759,769 A | 7/1988 | Hedman et al. | |
| 4,820,305 A | 4/1989 | Harms et al. | |
| 4,904,261 A | 2/1990 | Dove et al. | |
| 4,932,975 A | 6/1990 | Main et al. | |
| 5,026,373 A | 6/1991 | Ray et al. | |
| 5,052,373 A | 10/1991 | Michelson | |
| 5,059,194 A | 10/1991 | Michelson | |
| 5,062,850 A | 11/1991 | MacMillan et al. | |
| 5,108,395 A | 4/1992 | Laurain | |
| 5,116,338 A | 5/1992 | Poggie et al. | |
| 5,192,327 A | 3/1993 | Brantigan | |
| 5,236,460 A | 8/1993 | Barber | |
| 5,290,312 A | 3/1994 | Kojimoto et al. | |
| 5,336,223 A | 8/1994 | Rogers | |
| 5,405,391 A | 4/1995 | Hednerson et al. | |
| 5,413,602 A | 5/1995 | Metz-Stavenhagen | |
| 5,540,696 A | 7/1996 | Booth, Jr. et al. | |
| 5,571,190 A | 11/1996 | Ulrich et al. | |
| 5,571,192 A | 11/1996 | Schonhoffer | |
| 5,645,084 A | 7/1997 | McKay | |

(Continued)

FOREIGN PATENT DOCUMENTS

| | | |
|---|---|---|
| DE | 94 13 778 U1 | 1/1996 |
| DE | 195 09 317 A1 | 9/1996 |
| EP | 1 080 703 A2 | 3/2001 |
| FR | 2 636 227 | 3/1990 |

*Primary Examiner*—Eduardo C Robert
*Assistant Examiner*—Ellen C Hammond (57) ABSTRACT

A vertebral implant for insertion into a patient includes first and second end members that include recesses for engaging a spacer member and a distractor. The end plates include a bone contact surface and an oppositely facing surface. A peripheral surface extends around a perimeter of the end members. The recesses may extend inward from the oppositely facing surfaces. Further, the recesses may extend inward from the peripheral surfaces. The recesses for engaging the spacer member and distractor may be separate from each other or may intersect one another. A spacer may engage the end plates to establish a desired vertebral spacing. The spacer may be positioned between the implants after a desired distraction is obtained with a distractor that engages the end plates.

9 Claims, 10 Drawing Sheets

U.S. PATENT DOCUMENTS

| | | | |
|---|---|---|---|
| 5,702,451 A | 12/1997 | Biedermann et al. | |
| 5,702,453 A | 12/1997 | Rabbe et al. | |
| 5,702,455 A | 12/1997 | Sagger | |
| 5,776,197 A | 7/1998 | Rabbe et al. | |
| 5,776,198 A | 7/1998 | Rabbe et al. | |
| 5,897,556 A | 4/1999 | Drewry et al. | |
| 5,980,522 A | 11/1999 | Koros et al. | |
| 5,989,290 A * | 11/1999 | Biedermann et al. | 623/17.11 |
| 6,015,436 A | 1/2000 | Schonhoffer | |
| 6,086,613 A | 7/2000 | Camino et al. | |
| 6,106,557 A * | 8/2000 | Robioneck et al. | 623/17.15 |
| 6,113,638 A * | 9/2000 | Williams et al. | 128/898 |
| 6,126,660 A | 10/2000 | Dietz | |
| 6,159,211 A | 12/2000 | Boriani et al. | |
| 6,176,881 B1 | 1/2001 | Schar et al. | |
| 6,190,413 B1 | 2/2001 | Sutcliffe | |
| 6,193,720 B1 | 2/2001 | Yuan et al. | |
| 6,193,755 B1 | 2/2001 | Metz-Stavenhagen et al. | |
| 6,193,756 B1 | 2/2001 | Studer et al. | |
| 6,235,034 B1 | 5/2001 | Bray | |
| 6,296,647 B1 * | 10/2001 | Robioneck et al. | 606/105 |
| 6,296,665 B1 | 10/2001 | Strnad et al. | |
| 6,299,644 B1 | 10/2001 | Vanderschot | |
| 6,344,057 B1 | 2/2002 | Rabbe et al. | |
| 6,375,681 B1 | 4/2002 | Truscott | |
| 6,375,683 B1 | 4/2002 | Crozet et al. | |
| 6,395,034 B1 | 5/2002 | Suddaby | |
| 6,520,991 B2 | 2/2003 | Huene | |
| 6,569,168 B2 | 5/2003 | Lin | |
| 6,616,672 B1 | 9/2003 | Essiger | |
| 6,616,695 B1 | 9/2003 | Crozet et al. | |
| 6,645,249 B2 | 11/2003 | Ralph et al. | |
| 6,648,891 B2 | 11/2003 | Kim | |
| 6,660,038 B2 | 12/2003 | Boyer, II et al. | |
| 6,682,561 B2 * | 1/2004 | Songer et al. | 623/17.11 |
| 6,682,562 B2 | 1/2004 | Viart et al. | |
| 6,719,796 B2 | 4/2004 | Cohen et al. | |
| 6,758,862 B2 | 7/2004 | Berry et al. | |
| 6,776,798 B2 | 8/2004 | Camino et al. | |
| 6,808,538 B2 | 10/2004 | Paponneau | |
| 6,899,734 B2 | 5/2005 | Castro et al. | |
| 6,899,735 B2 * | 5/2005 | Coates et al. | 623/17.16 |
| 6,908,485 B2 | 6/2005 | Crozet et al. | |
| 6,929,662 B1 | 8/2005 | Messerli et al. | |
| 7,060,073 B2 | 6/2006 | Frey et al. | |
| 2002/0045904 A1 | 4/2002 | Fuss et al. | |
| 2002/0049444 A1 | 4/2002 | Knox | |
| 2002/0123754 A1 | 9/2002 | Holmes et al. | |
| 2003/0083746 A1 | 5/2003 | Kuslich | |
| 2003/0167059 A1 | 9/2003 | Young | |
| 2003/0191531 A1 | 10/2003 | Berry et al. | |
| 2004/0106999 A1 | 6/2004 | Mathews | |
| 2004/0181283 A1 | 9/2004 | Boyer et al. | |
| 2004/0186569 A1 * | 9/2004 | Berry | 623/17.11 |
| 2004/0199252 A1 | 10/2004 | Sears et al. | |
| 2005/0004572 A1 | 1/2005 | Biedermann et al. | |
| 2005/0113924 A1 | 5/2005 | Buttermann | |
| 2005/0159814 A1 | 7/2005 | Karahalios | |
| 2005/0216088 A1 | 9/2005 | McKinley et al. | |
| 2006/0052870 A1 | 3/2006 | Ferree | |
| 2006/0095134 A1 * | 5/2006 | Trieu et al. | 623/17.16 |

* cited by examiner

EXPANDABLE VERTEBRAL BODY IMPLANTS AND METHODS OF USE

BACKGROUND

Spinal implants are often used in the surgical treatment of spinal disorders such as degenerative disc disease, disc herniations, scoliosis or other curvature abnormalities, and fractures. Many different types of treatments are used, including the removal of one or more vertebral bodies and/or intervertebral disc tissue. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Regardless of the type of treatment and the type of implant used, surgical implantation tends to be a difficult for several reasons. For instance, access to the affected area may be limited by other anatomy. Further, a surgeon must be mindful of the spinal cord and neighboring nerve system. The size of the implant may present an additional obstacle. In some cases, a surgeon may discover that an implanted device has an inappropriate size for a particular application, which may require removal of the implant and insertion of a different implant. This trial and error approach may increase the opportunity for injury and is certainly time-consuming. Expandable implants are becoming more prevalent as a response to some of these concerns. However, the expansion mechanism in these devices tends to be complex and large. Consequently, existing devices do not appear to address each of these issues in a manner that improves the ease with which the device may be surgically implanted.

SUMMARY

Illustrative embodiments disclosed herein are directed to a vertebral implant for insertion between vertebral bodies in a patient. The implant generally includes first and second end members that include recesses for engaging a spacer member and a distractor. The end plates include a bone contact surface and an oppositely facing surface. A peripheral surface extends around a perimeter of the end members. The recesses may extend inward from the oppositely facing surfaces. Further, the recesses may extend inward from the peripheral surfaces. The recesses for engaging the spacer member and distractor may be separate from each other or may intersect one another. A spacer may engage the end plates to establish a desired vertebral spacing. A surgeon may select a spacer having a desired height from among a set of spacers, each including a different height. Alternatively, the spacer may be expandable in a distraction direction. The spacer may be positioned between the implants after a desired distraction is obtained with a distractor that engages the end plates. Advantageously, the spacer and the distractor may engage the appropriate recess in the end members through the peripheral surface to avoid over-distraction of the vertebral bodies.

DETAILED DESCRIPTION

The various embodiments disclosed herein relate to a vertebral implant in which multiple components may be combined to establish a desired spacing between vertebral bodies in a patient. Advantageously, the implant components may be inserted at different times or in a compressed state with the components adjusted to the desired spacing in situ. Reference number 10 in FIG. 1 generally identifies an exemplary implant. In one embodiment, the implant 10 is positionable within an intervertebral space S to span one or more vertebral levels along the longitudinal axis of the spinal column. Although the illustrated embodiment of the implant 10 spans one vertebral level, it should be understood that the implant 10 may be configured to span multiple vertebral levels, including two or more vertebral levels.

Figure 1:
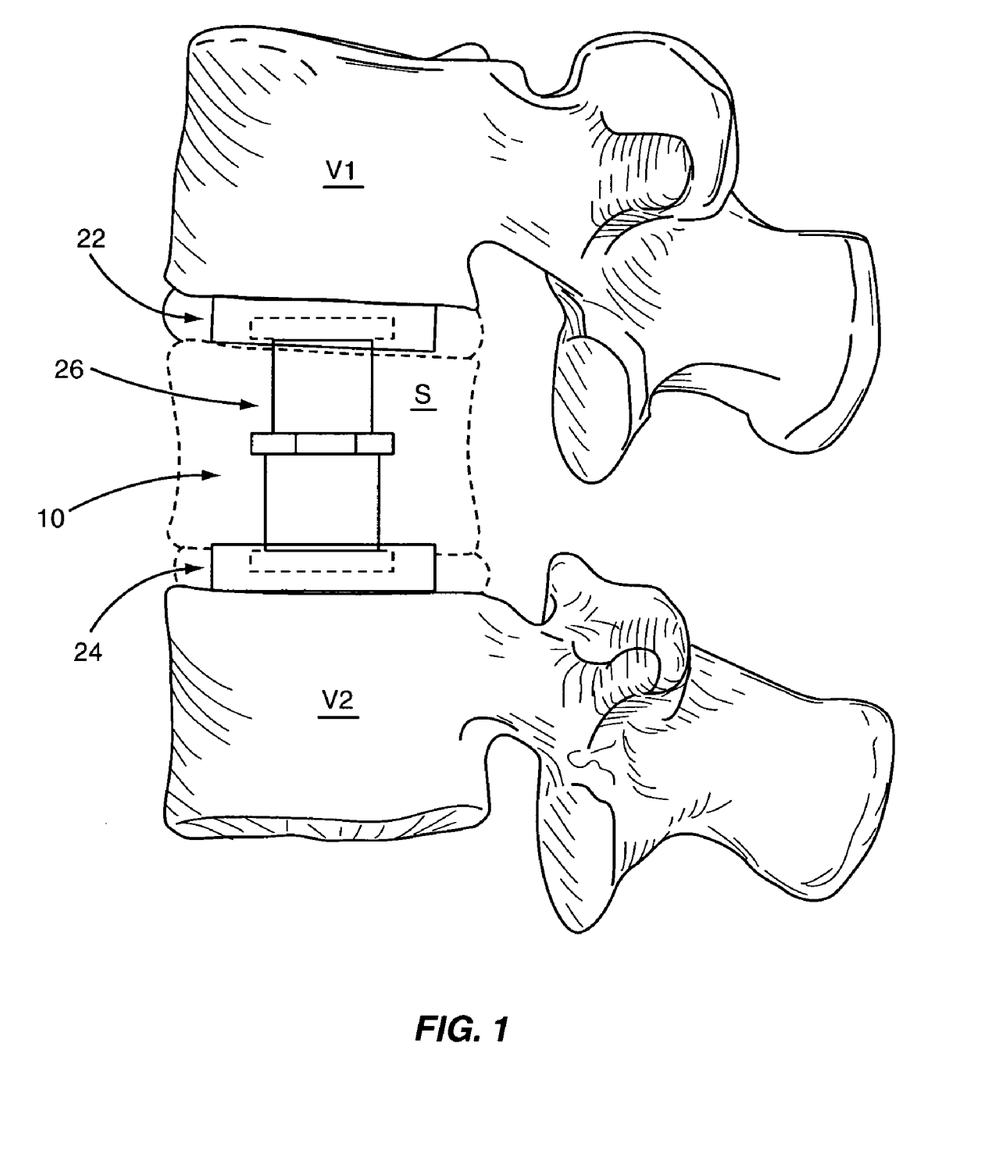
FIG. 1 is a lateral view of a vertebral implant according to one or more embodiments shown relative to vertebral bodies.

The implant 10 generally includes a first end member 22, a second end member 24, and one or more spacer members 26 coupled between the first and second end members 22, 24. In the illustrated embodiment, end member 22 is disposed in a superior position relative to an inferior opposite end member 24. In one embodiment, the end members 22, 24 and spacer member 26 are formed of a biocompatible material, such as, for example, a carbon fiber material, or non-metallic substances, including polymers or copolymers made from materials such as PEEK and UHMWPE. In further embodiments, the end members 22, 24 and spacer member 26 may be formed of other suitable biocompatible materials, such as, for example, stainless steel, titanium, cobalt-chrome, and shape memory alloys.

The end members 22, 24 are adapted to engage the endplates of upper and lower vertebral bodies V1, V2. The spacer member 26 is engaged between the end members 22, 24 to maintain an intervertebral axial space S between the upper and lower vertebral bodies V1, V2 following the removal of one or more vertebral levels (shown in phantom). To facilitate insertion of the implant 10, the spacer member 26 may be inserted separately from the end members 22, 24. That is, the end members 22, 24 may be inserted during a first insertion step and the spacer member 26 may be inserted during a second, subsequent insertion step. Further details regarding exemplary insertion steps are provided below.

Figure 2:
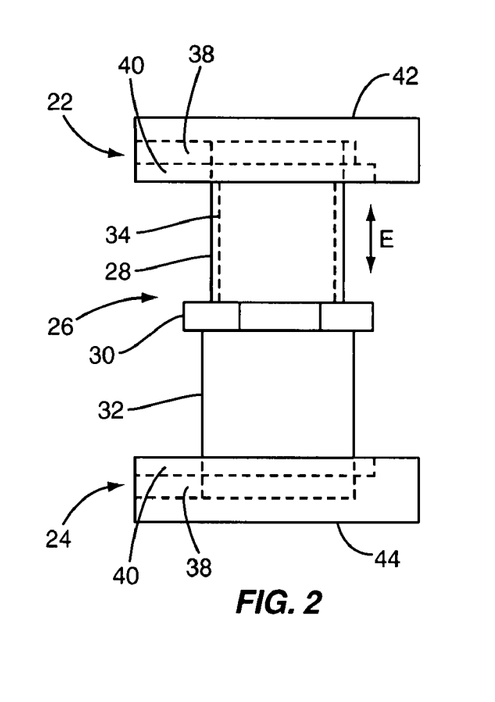
FIG. 2 is a lateral view of a vertebral implant according to one or more embodiments.

FIG. 2 shows an exemplary implant 10 including the end members 22, 24 and the spacer member 26 disposed therebetween. The spacer member 26 may have a fixed or adjustable height. In the illustrated embodiment, the spacer member 26 includes an extendable portion 28 that is adjustable in a longitudinal direction as illustrated by the arrows labeled E. The exemplary spacer member 26 is expandable in a direction that is substantially transverse to the bone contact surfaces 42, 44 of the end members 22, 24. In one embodiment, the extendable portion 28 is movable relative to an outer portion 32. The extendable portion 28 may include threads 34 that engage with a rotatable collar 30. The rotatable collar 30 is rotatably coupled to the outer portion 32 such that rotation of the collar 30 produces a corresponding extension or retraction of the extendable portion 28. Certainly, other types of extendable spacer members 26 may be used. Those skilled in the art will appreciate that other types of mechanical spacers may be used. Similarly, other spacers may implement pneumatic, hydraulic, or electric power to extend from a first compressed height to a desired second height to attain the desired amount of vertebral distraction.

Figure 3:
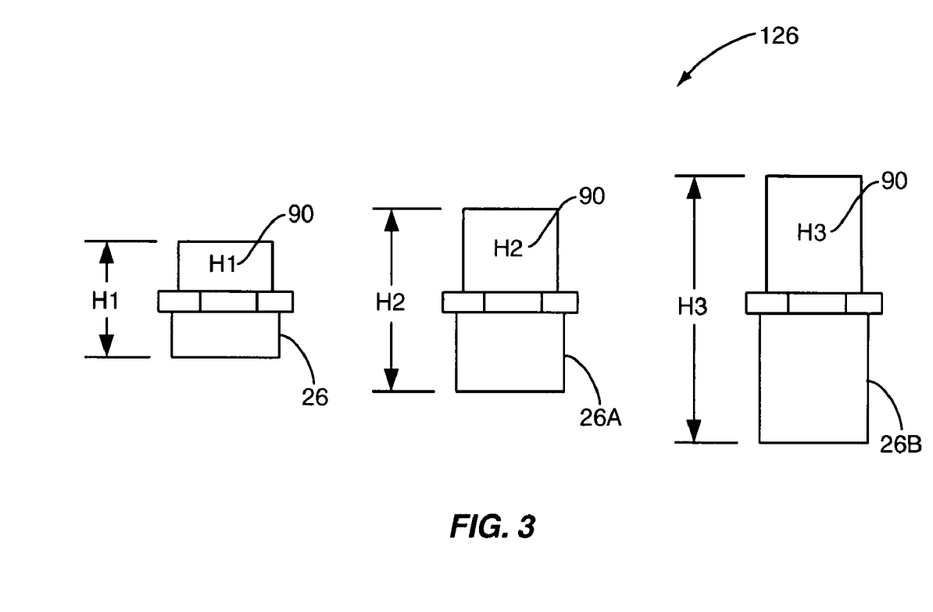
FIG. 3 depicts lateral views of a set of spacer members, each including a different height, of a vertebral implant according to one embodiment.

In one embodiment, the spacer member 26 includes a fixed height. Thus, as FIG. 3 shows, spacer members 26, 26A, 26B and so on may belong to a set of spacer members 126, with each spacer member 26, 26A, 26B including a different height H1, H2, H3. As the parts are formed, the measurable height H1, H2, H3 may be indicated as a marking 90 on the exterior of the spacer member 26, 26A, 26B to provide surgeons an indication of the relative height of the spacer members 26, 26A, 26B. This marking may be provided as an alphanumeric indication as represented by the letters H1, H2, H3 in FIG. 3. The marking may include an actual height in inches or millimeters. The marking may include a relative indication of the height of the spacer within the set 126. For instance, the spacer members 26, 26A, 26B may be marked in ascending numerical or alphabetical characters. The marking may be stamped, whether by ink or metal deformation, engraved, or otherwise displayed on the spacer members 26, 26A, 26B.

During implantation, a surgeon may select a spacer member 26, 26A, 26B from the set based upon an estimated or calculated desirable implant height. This estimation or calculation may be based at least partly upon radiograph information, the patient size and age, and the location of the implanted device 10. However, during such a procedure, a surgeon may determine that a different size is desirable. For instance, the surgeon may determine that a slightly smaller or larger implant height is desirable. Accordingly, the surgeon may remove a first implanted spacer member 26, 26A, 26B in favor of a more appropriate spacer member 26, 26A, 26B from the overall set 126.

Figure 4:
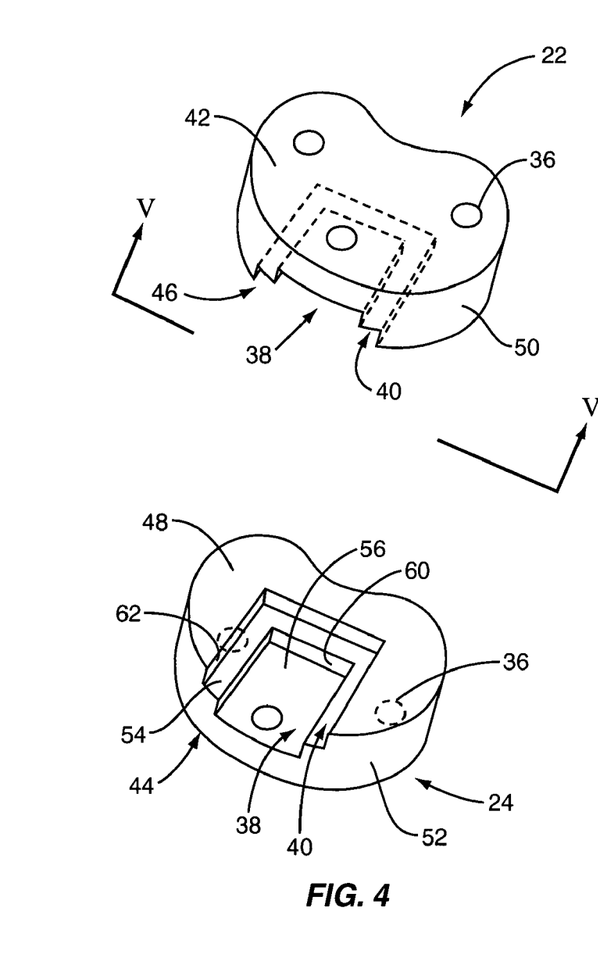
FIG. 4 is a perspective view of end members of a vertebral implant according to one embodiment.

As suggested, the spacer member 26 is separable from the end members 22, 24. To illustrate this characteristic, FIG. 4 shows the end members 22, 24 in perspective view with the spacer member 26 removed. In the illustrated embodiment, the end members 22, 24 include a kidney shape, though other shapes may be used. In further embodiments, the end members 22, 24 may take on other types of configurations, such as, for example, a circular shape, semi-oval shape, bean-shape, D-shape, elliptical-shape, egg-shape, or any other shape that would occur to one of skill in the art. The end members 22, 24 may take on substantially solid configurations, such as, for example, block-like or plate-like configurations that do not define an open inner region. In other embodiments, the end members 22, 24 could also be described as being annular, U-shaped, C-shaped, V-shaped, horseshoe-shaped, semi-circular shaped, semi-oval shaped, or other similar terms defining an implant including at least a partially open or hollow construction.

The end members 22, 24 include respective bone-contact surfaces 42, 44. Each end member 22, 24 further includes an opposing surface 46, 48 that faces towards the spacer member 26 when inserted between the end members 22, 24. A peripheral wall 50, 52 extends about the perimeter of the end members 22, 24 between the respective bone contact surfaces 42, 44 and opposing, non-bone contact surfaces 46, 48. Note that the peripheral wall 50, 52 may be part of one or both the bone contact surfaces 42, 44 and opposing surfaces 46, 48, such as where the surfaces blend into one another. Thus, there is no express requirement that there be a sharp edge between the bone contact surfaces 42, 44, the peripheral surfaces 50, 52, or the opposing surfaces 46, 48 as illustrated.

In one embodiment, the end members 22, 24 have an outer profile that is substantially complementary to the size and shape of the peripheral portion or outlying region of the vertebral bodies V1, V2, such as the cortical rim or the apophyseal ring of the vertebral endplates. In this manner, some portion of the bone contact surfaces 42, 44 of end members 22, 24 may be engaged against the cortical region of the vertebral endplates, thereby minimizing the likelihood of subsidence into the relatively softer cancellous region of the vertebral bodies V1, V2 following insertion of the implant 10 within the intervertebral space S.

Additionally, the exemplary end members 22, 24 include one or more apertures 36 disposed about the bone contact surfaces 42, 44. The apertures 36 may have different size, quantity, and location that those illustrated. The apertures 36 may be blind holes in that they do not extend through the end members 22, 24. The apertures 36 may be through-holes in that they do extend through the end members 22, 24. The end members 22, 24 may be inserted in conjunction with bone growth materials (not shown) that may include, for example, bone graft, bone morphogenetic protein (BMP), allograft, autograft, and various types of cement, growth factors and mineralization proteins. These bone growth materials may be packed into the apertures 36 to promote osseointegration of the end members 22, 24 to the vertebral bodies V1, V2. In a further embodiment, the bone growth promoting materials may be provided in a carrier (not shown), such as, for example, a sponge, a block, a cage, folded sheets, or paste that may be inserted into the apertures 36.

Figure 5:
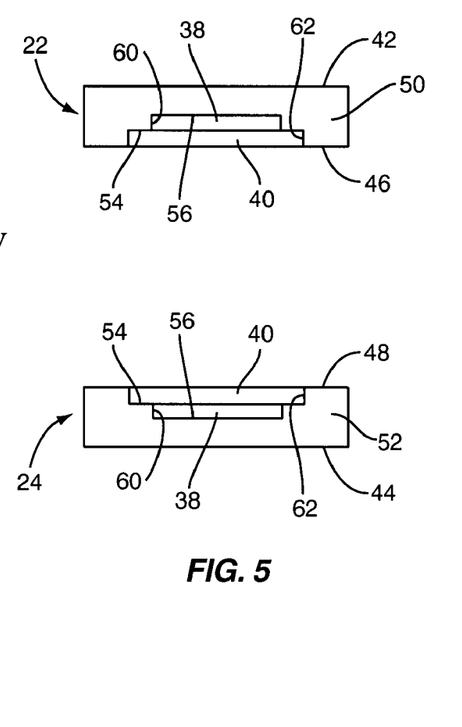
FIG. 5 is a lateral view of end members of a vertebral implant according to one embodiment.

The end members 22, 24 include a spacer recess 38 that is sized and shaped to accept the spacer member 26. Each member 22, 24 may have a similarly formed spacer recess 38. Alternatively, end member 22 may have a spacer recess 38 that is different in size or shape than a corresponding spacer recess 38 in the opposite end member 24. Each end member 22, 24 further includes a distractor recess 40 that is sized and shaped to accept a distractor as discussed below. In short, a distractor (see e.g., FIGS. 7-11) may be used to establish a desired spacing and/or a desired amount of distraction between the end members 22, 24 prior to inserting the spacer member 26 into the spacer recesses 38. In the embodiment illustrated, the spacer recess 38 and the distractor recess 40 extend inward from the outer peripheral surfaces 50, 52. In the exemplary embodiment, the spacer recess 38 and the distractor recess 40 extend substantially parallel to the bone contact surfaces 42, 44. In certain other implementations, the bone contact surfaces 42, 44 are not necessarily planar and may include curvatures or angled orientations relative to the longitudinal axis of the spine. In these types of end members 22, 24, the spacer recess 38 and the distractor recess 40 may extend inward from the outer peripheral surface 50, 52 in a direction that coincides with an insertion direction for the spacer member 26. That is, the spacer member 26, if fully extended to a desire height (or including a desired fixed height), may be inserted into the end members 22, 24 without having to over-distract the end members 22, 24. Note that FIG. 5 is shown according to the view lines provided in FIG. 4 and that this direction coincides with the spacer member 26 insertion direction. This direction may also coincide with a distractor (as in FIGS. 7-11) insertion and removal direction.

Figure 6:
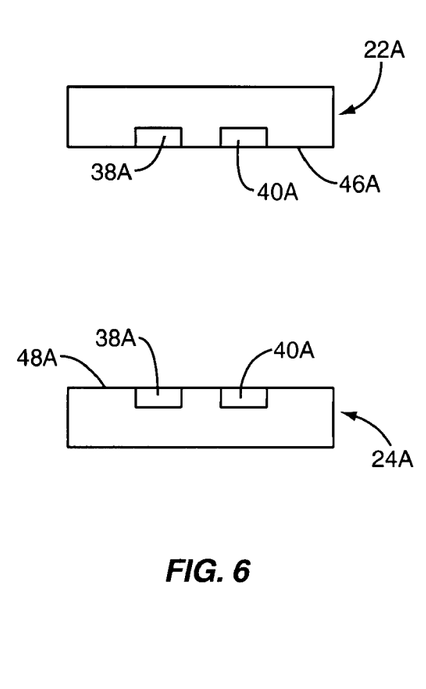
FIG. 6 is a lateral view of end members of a vertebral implant according to one embodiment.

FIG. 5 illustrates that the spacer recess 38 and the distractor recess 40 intersect one another and occupy much of the same volume. FIG. 5 further suggests that the spacer recess 38 extends a greater depth from the respective non-bone-contact surfaces 46, 48 of the end members 22, 24 than the distractor recess surface 40. Specifically, the spacer recess 38 terminates at a spacer abutment surface 56. The distractor recess 40, on the other hand, terminates at a distractor abutment surface 54. Lateral side 60 further defines the spacer recess 38 while lateral side 62 further defines the distractor recess 40. In the present embodiment, lateral side 62 is disposed outside of lateral side 60. As described below, this stair-stepped configuration permits the spacer member 26 and a distractor to remain simultaneously engaged to different portions of the end members 22, 24. In an alternative embodiment, the spacer recess 38A and distractor recess 40A are separate from one another as depicted in FIG. 6. Similar to the embodiment in FIG. 5, the spacer recess 38A and distractor recess 40A extend inward from the respective peripheral walls 50A, 52A and the respective non-bone-contact surfaces 46A, 48A.

In one embodiment as illustrated in FIGS. 4 and 5, the end member 24 is a second end member. The outer peripheral surface 52 is part of an intermediate wall that extends between surfaces 44, 48. The spacer recess 38 and distractor recess 40 form a second receptacle. The spacer abutment surface 56 forms a bottom wall that defines a depth of the second receptacle. The distractor abutment surface 54 forms a ledge positioned between the bottom wall and the surface 48. The ledge is uncovered in a direction directly towards the first member. In another embodiment, the end member 22 is a second end member and includes these similar elements.

Figure 7:
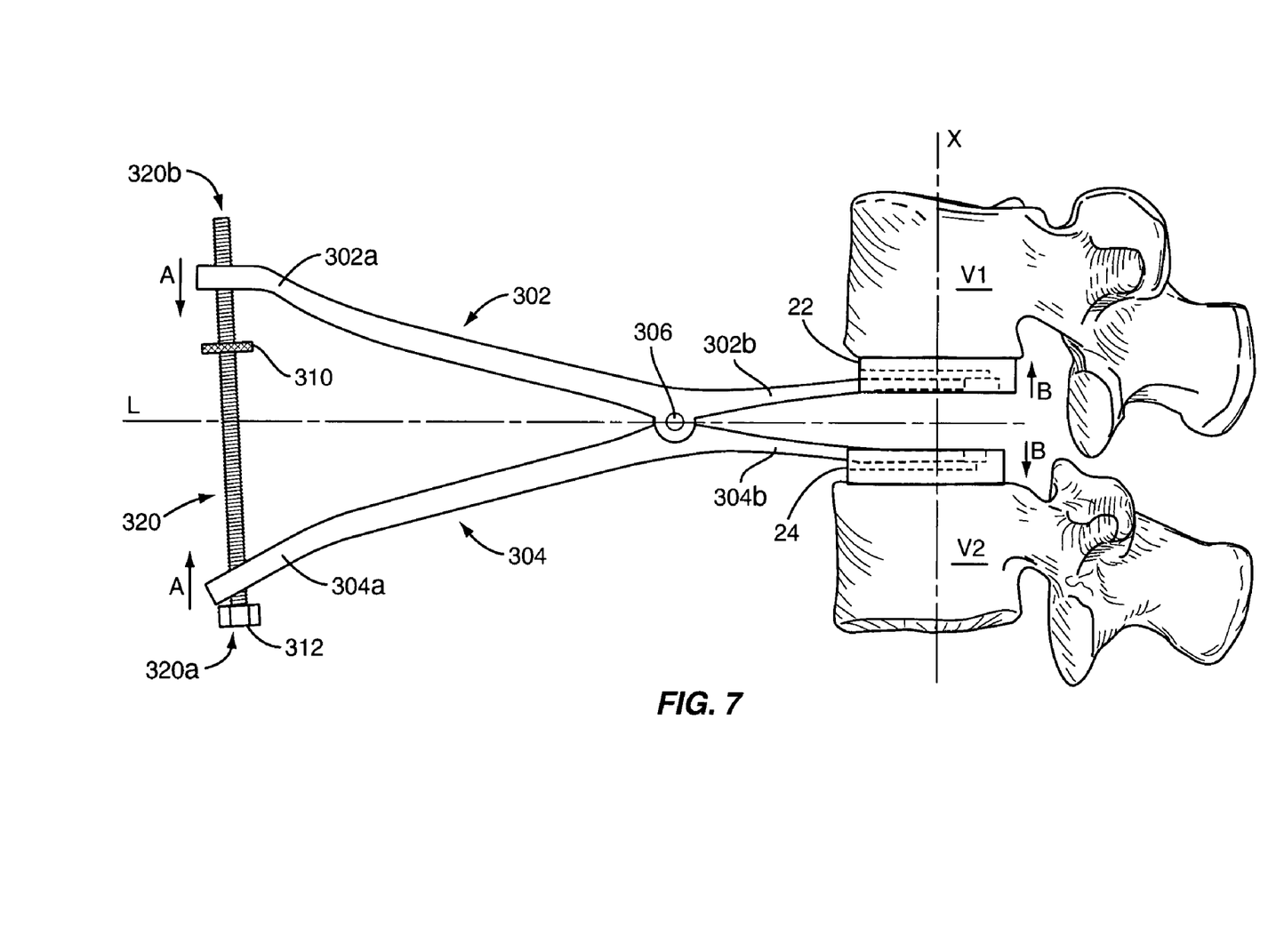
FIGS. 7-10 illustrate a sequence of implantation steps to obtain a desired vertebral body spacing, each Figure depicting a lateral view of a distractor and components of a vertebral implant according to one or more embodiments shown relative to vertebral bodies.

The implant 10 may be inserted into a patient according to the process steps illustrated in FIGS. 7-10. In FIG. 7, the end members 22, 24 are inserted and positioned within an intervertebral space formed after the removal of one or more vertebrae or discs. Next, a distractor 100 is inserted into the respective distractor recesses 40 in the end members 22, 24. The exemplary distractor 300 extends along a longitudinal axis L and generally includes a first distractor arm 302 and a second distractor arm 304. The first and second distractor arms 302, 304 are coupled to one another via a hinge mechanism 306 which provides for pivotal movement between the distractor arms 302, 304 about the hinge mechanism 306. As should be appreciated, an inward compression force exerted onto the proximal portions 302a, 304a of the distractor arms in the direction of arrows A will cause the distal end portions 302b, 304b to be outwardly displaced in the direction of arrows B. Thus, distraction of the vertebral bodies V1, V2 is achieved along longitudinal axis X, which corresponds at least generally with the longitudinal axis of the spine and of the implant 10.

In the illustrated embodiment, the distractor 300 includes a threaded rod 320 having a first end portion 320a rotatably coupled with the proximal end portion 304a of the distractor arm 304, and a second end portion 320b engaged within a threaded aperture (not specifically shown) extending through the proximal end portion 302a of the distractor arm 302. As should be appreciated, the position of rod 320 may be adjusted relative to the distractor arm 302 by threading the rod 320 with a rotary knob 312 to correspondingly control the amount of distraction provided by the distractor arms 302, 304. In one embodiment, the distractor 300 is provided with a gauge or stop member 310 that is adapted to limit outward displacement of the distal end portion 302b, 304b, which in turn correspondingly limits that amount of distraction provided by the distractor arms 302, 304. In this manner, over distraction of the intervertebral space S is avoided.

Figure 8:
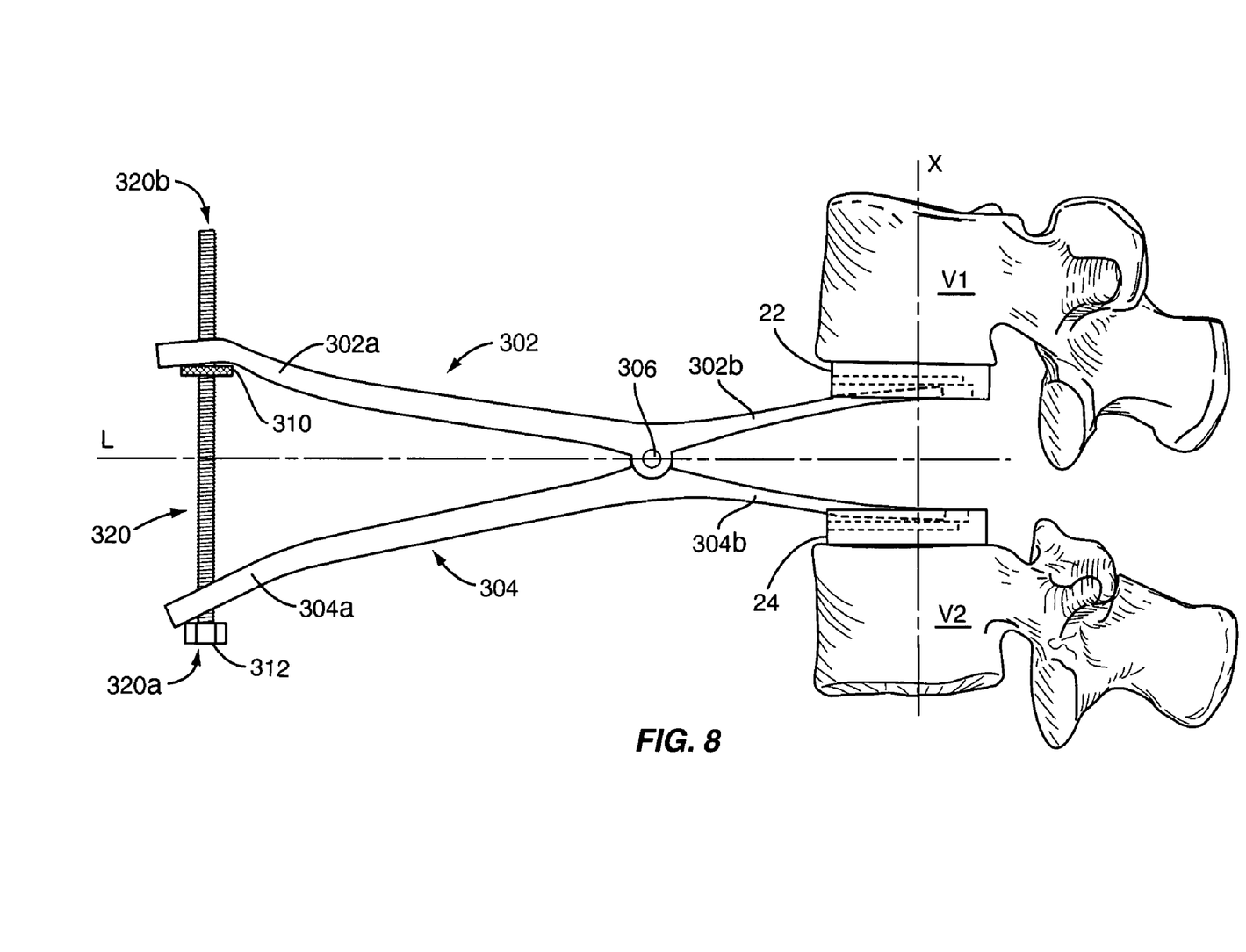
Figure 9:
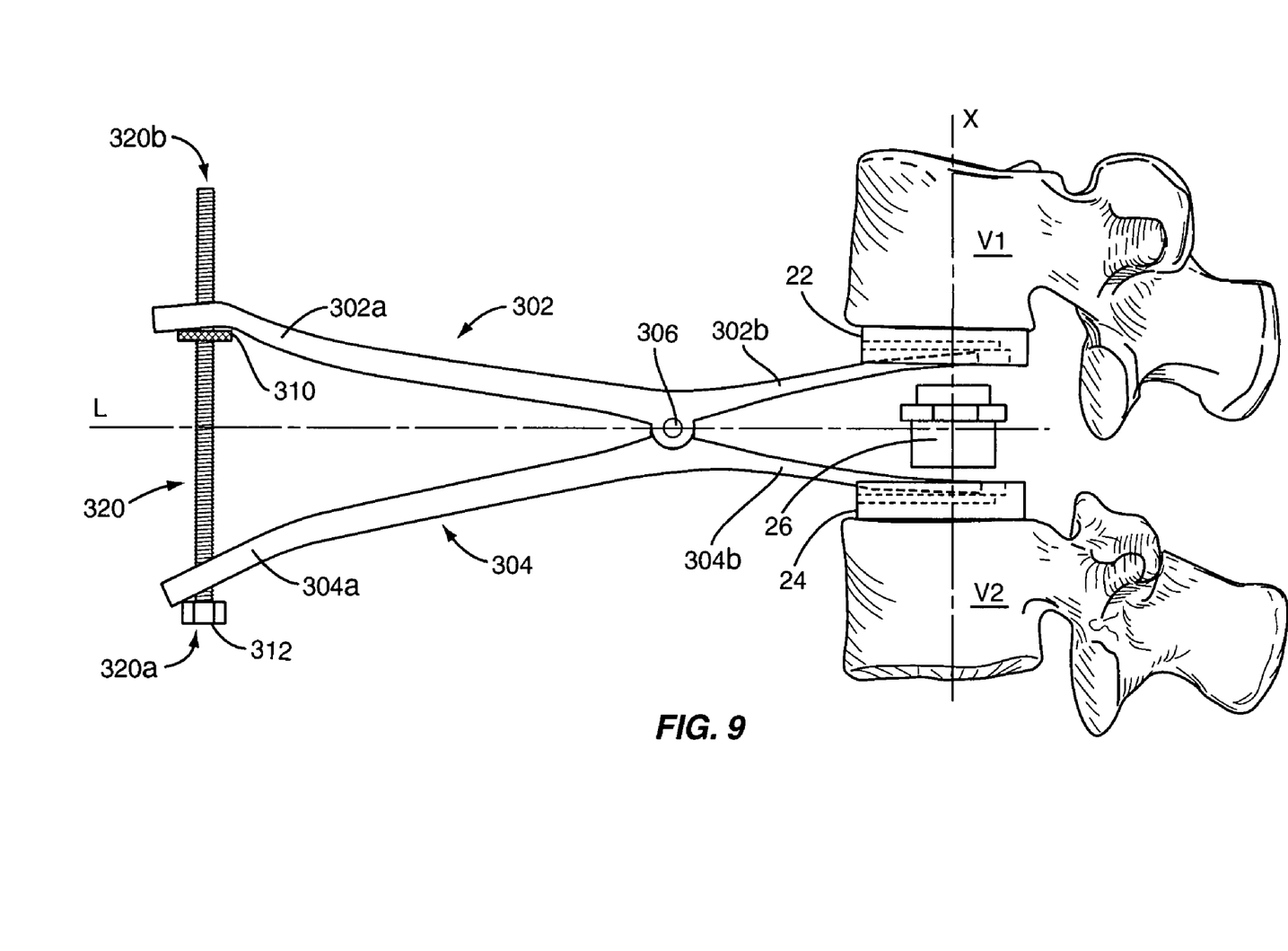
Figure 10:
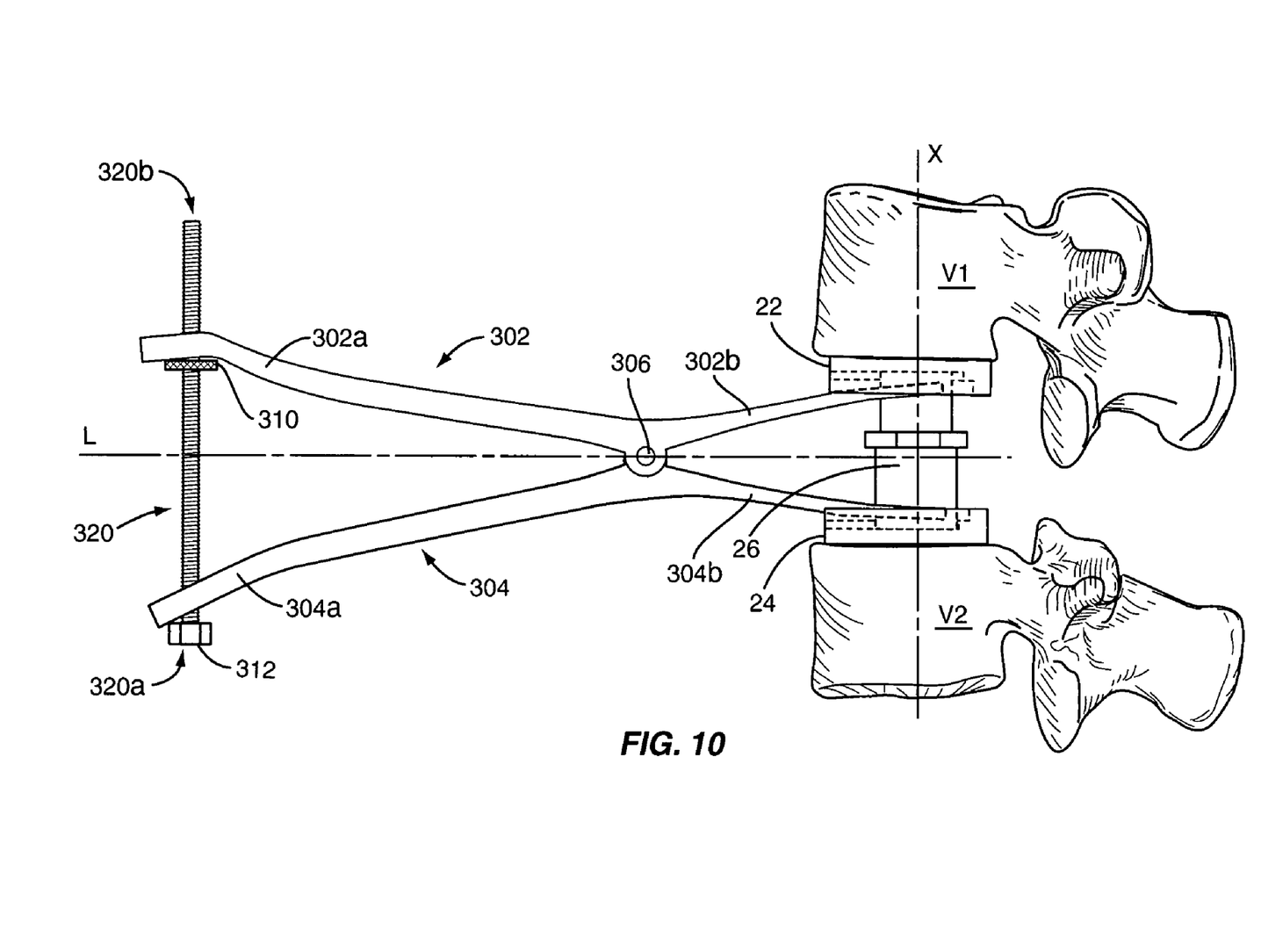
Figure 11:
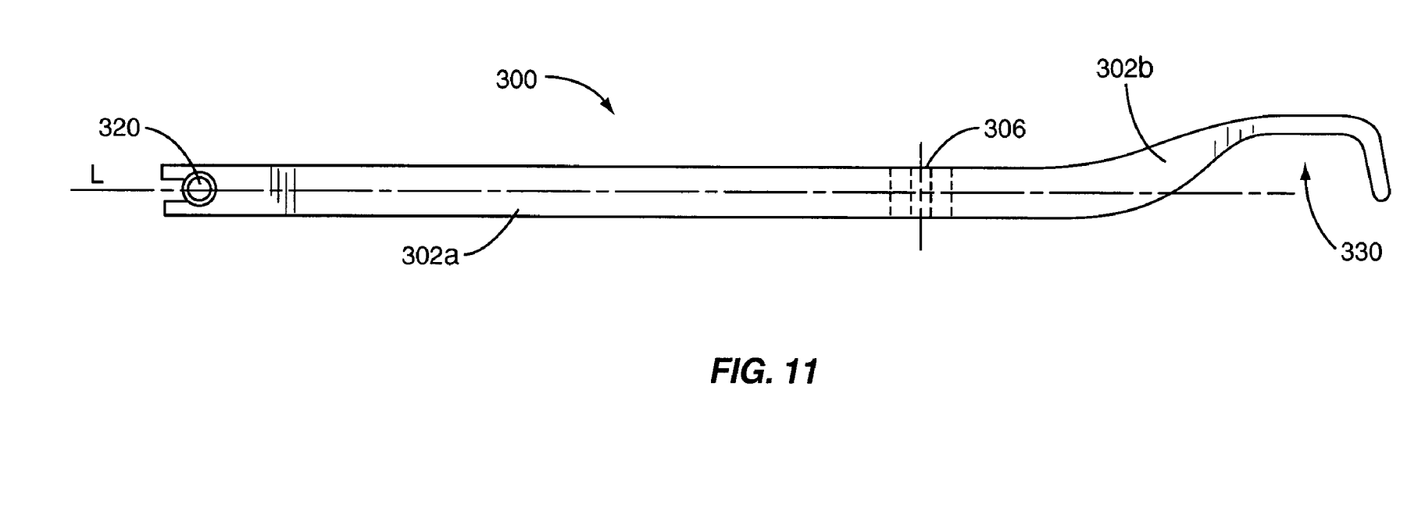
FIG. 11 depicts a top view of a distractor according to one embodiment.

The distal end of the distal end portions 302b, 304b include geometry that engages the distractor recesses 40 of the end members 22, 24. FIG. 11 depicts a top view of the exemplary distractor 300. In one embodiment, the distal end portions 302b, 304b of the distractor arms 302, 304 define a lateral offset relative to the longitudinal axis L. Further, the distal end portions 302b, 304b include an arcuate-shaped configuration defining a C-shaped lateral offset. However, other shapes and configurations of the distal end portions 302b, 304b are also contemplated. The shape of the distal end portions 302b, 304b define an open area 330 that is sized to fit around a spacer member 26, which may be inserted after the end members 22, 24 are distracted a desired amount as shown in FIGS. 8-10. Notably, FIGS. 7-10 illustrate one particular type of distractor 300 that uses a threaded rod 320 to achieve a mechanical advantage and distract the vertebral bodies V1, V2 a desired amount. However, those skilled in the art will appreciate that different types of distractors may be used, including but not limited to devices incorporating pneumatic, hydraulic, electrical, or mechanical displacement forces. However, it is generally contemplated that the distractor (300 or otherwise) include engaging features with a size and shape that engages the distractor recesses 40, yet provides access to the spacer recess 38 while the distractor 300 is engaged with the distractor recesses 40 as described herein.

With the distractor 300 engaged in the distractor recesses 40 as shown in FIG. 7, the rotary knob 312 may be rotated to force the distal end portions 302b, 304b in the direction of arrows B. FIG. 8 shows the proximal ends 302a, 304a in closer proximity to one another. Correspondingly, the distal ends 302b, 304b are spaced farther apart compared to the position shown in FIG. 7. With the desired amount of distraction achieved, the distractor 300 may be maintained in the position shown and the spacer member 26 introduced into the space formed between the end members 22, 24 as shown in FIG. 9. In one implementation, the spacer member 26 is expandable and may be extended to the position shown in FIG. 10. However, in another implementation, the spacer member 26 includes a fixed height and may be introduced into the spacer recess 38 as described above. That is, since the end members 22, 24 include a spacer recess 38 that is accessible from the peripheral walls 50, 52, additional distraction is not required. Furthermore, because the distractor 300 includes the open configuration shown in FIG. 11, the spacer member 26 may be introduced into the end members 22, 24 while the distractor 300 engages and maintains the desired amount of distraction through engagement with the respective distractor recesses 40.

Once the spacer member 26 is seated as desired in the spacer recesses 38, the distractor 300 may be disengaged along the longitudinal axis L. Again, since the distractor recess 40 is open to the peripheral walls 50, 52 of the end members 22, 24, the distractor 300 does not necessarily have to be compressed by turning the rotary knob 312 prior to removal. Once the distractor 300 is removed, the implant 10 remains in the vertebral space S as shown in FIG. 1.

Figure 12:
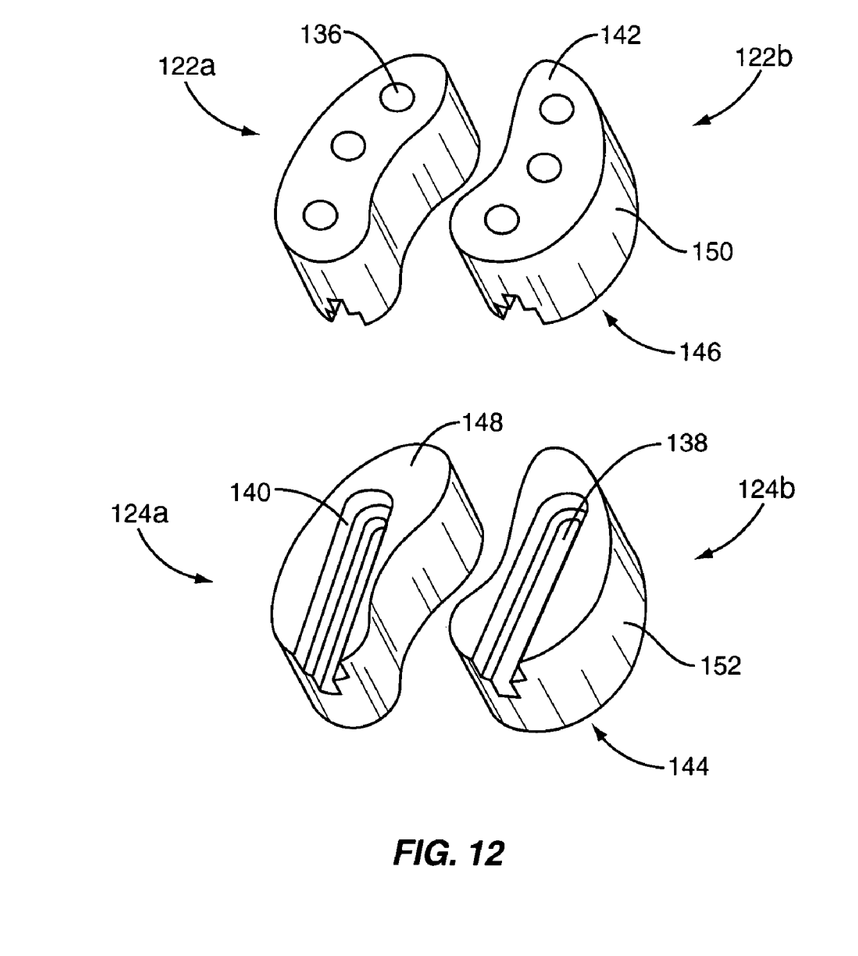
FIG. 12 is a perspective view of end members of a vertebral implant according to one embodiment.

The embodiments described above have contemplated a vertebral implant 10 including one end member 22, 24 at each end of a spacer member 26. Further, the insertion of the implant 10 has been depicted using an exemplary anterior approach as is known in the art. However, other implant devices may be inserted using known posterior or trans-foraminal approaches. Accordingly, the end members 122a, 122b, 124a, 124b shown in FIG. 12 may be incorporated in an implant inserted using posterior or lateral approaches. The exemplary end members 122a, 122b, 124a, 124b include features similar to the above-describe embodiments, including bone-contact surfaces 142, 144, opposing non-bone-contact surfaces 146, 148, peripheral surfaces 150, 152, bone-growth apertures 136, spacer recesses 138 and distractor recesses 140. The function and characteristics of these features may be similar to those described above, with the size and shape of the features modified according to the different size of the end members 122*a*, 122*b*, 124*a*, 124*b*.

Figure 13:
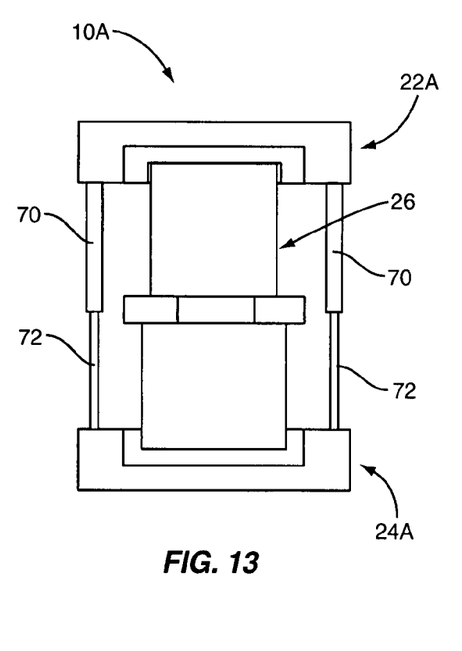
FIG. 13 is a lateral view of a vertebral implant according to one or more embodiments.

The end members 22, 24 described above were embodied as separate members. In embodiments depicted in FIGS. 13, 14, and 15, the end members are coupled to one another to ease installation. In the illustrated embodiments, most features of the end members 22, 24, and spacer member 26 are similar to that described above. However, in the embodiments of FIGS. 13-15, each end member is coupled to one or more attachment members. For instance, in FIG. 13, the end members 22A, 24A of implant 10A include sliding and telescoping attachment members 70, 72, respectively. In one embodiment, the attachment members 70, 72 are rigid and capable of axially sliding relative to one another. Further, because the attachment members 70, 72 are rigid, the end members 22A, 24A are maintained in a predetermined alignment relative to each other. In one embodiment, attachment members 70, 72 are flexible members that are capable of axially sliding relative to one another. Consequently, the end members 22A, 24A remain coupled, but are movable relative to each other in multiple directions.

Figure 14:
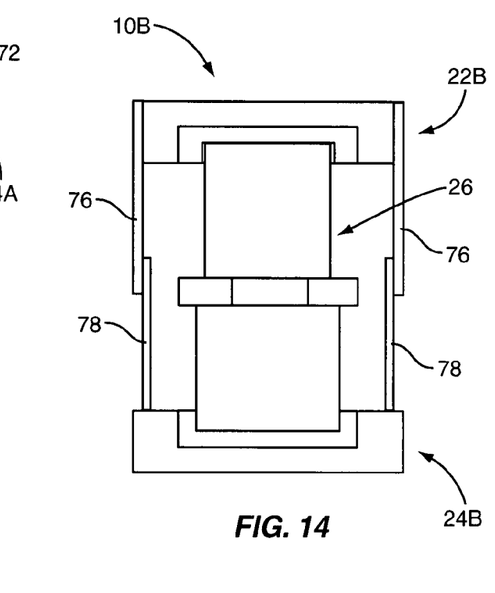
FIG. 14 is a lateral view of a vertebral implant according to one or more embodiments.
Figure 15:
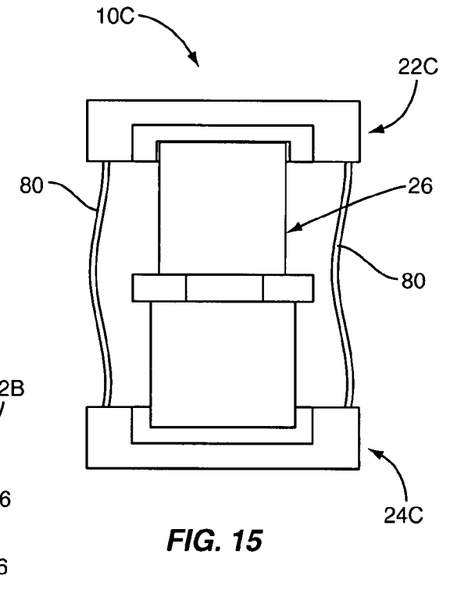
FIG. 15 is a lateral view of a vertebral implant according to one or more embodiments.

FIG. 14 depicts an embodiment of an implant 10B that includes attachment members 76, 78 extending respectively from the end members 22B, 24B. The attachment members 76, 78 are disposed in sliding contact with one another and permit relative movement between the end members 22B, 24B in an extension direction. However, the attachment members 76, 78 prevent relative lateral motion between the end members 22B, 24B. FIG. 15 depicts an embodiment of an implant 10C that includes flexible attachment members 80 that are coupled between the end members 22C, 24C. In one embodiment, the attachment members 80 are tethers that permit motion of the end members 22C, 24C relative to each other in multiple directions. The attachment member 80 may be implemented as braided cable, including metal or non-metal materials, tubing, or other suitable variants and may include fewer or greater numbers of attachment members 80 than that depicted in FIG. 15.

Furthermore, embodiments disclosed above have not included any particular surface geometry, coating, or porosity as are found in conventionally known vertebral implants. Surface features such as these are used to promote bone growth and adhesion at the interface between an implant and a vertebral end plate. Examples of features used for this purpose include, for example, teeth, scales, keels, knurls, and roughened surfaces. Some of these features may be applied through post-processing techniques such as blasting, chemical etching, and coating, such as with hydroxyapatite. The bone interface surfaces, including the osteoconductive inserts, may also include growth-promoting additives such as bone morphogenetic proteins. Alternatively, pores, cavities, or other recesses into which bone may grow may be incorporated via a molding process. Other types of coatings or surface preparation may be used to improve bone growth into or through the bone-contact surfaces. However, the inserts that include these types of features may still be formed and characterized by the aspects disclosed herein.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the end member embodiments disclosed herein have included a single spacer recess and a single distractor recess. In alternative implementations, each end member may include multiple spacer recesses or multiple distractor recesses for implementation in different locations or different implantation procedures. The present embodiments are, therefore, to be considered in all respects as illustrative and not restrictive, and all changes coming within the meaning and equivalency range of the appended claims are intended to be embraced therein.

What is claimed is:

1. A vertebral implant for insertion between vertebral bodies in a patient, the vertebral implant comprising:
a first end member and a second end member, each end member including a bone contact surface to contact an endplate of one of the vertebral bodies, an opposing surface, and a perimeter surface extending between the bone contact surface and the opposing surface, the end members further comprising a spacer recess and a distractor recess extending inward from the perimeter surface and the opposing surface, the end members being separated by a gap; and
a spacer member disposed within the gap between the end members and having opposing ends that engage the spacer recesses of the first and second end members;
the implant including a longitudinal axis that extends through the first and second end members and the spacer, the distractor recess including a greater width measured perpendicular to the longitudinal axis than the spacer recess with the distractor recesses extending outward beyond the spacer recess in a direction perpendicular to the longitudinal axis and open into the gap in a direction parallel to the longitudinal axis.

2. The vertebral implant of claim 1 wherein the spacer recess and the distractor recess are separate from one another.

3. The vertebral implant of claim 1 wherein the spacer recess and the distractor recess intersect one another.

4. The vertebral implant of claim 1 wherein the first end member and the second end member are coupled to one another.

5. The vertebral implant of claim 1 wherein the spacer implant includes a fixed height.

6. The vertebral implant of claim 1 wherein the spacer implant includes an adjustable height.

7. A vertebral implant for insertion between vertebral bodies in a patient, the vertebral implant comprising:
a first end member and a second end member, each end member including a bone contact surface to contact an endplate of one of the vertebral bodies, an opposing surface, and a perimeter surface extending therebetween, each of the end members further comprising a spacer recess and a distractor recess extending inward from the perimeter surface and the opposing surface, the spacer recess and the distractor recess intersecting one another along a longitudinal axis of the implant with the distractor recess being wider than the spacer recess in a direction perpendicular to the longitudinal axis to form a ledge at a bottom of the distractor recess, the spacer recess including an abutment surface opposite from the opposing surface and being spaced farther from the opposing surface than the ledge, the ledge being uncovered in a direction parallel with the longitudinal axis;

a spacer member positionable between the end members and having opposing ends sized to engage the spacer recesses of the first and second end members and space apart the first and second end members.

8. A vertebral implant for insertion between vertebral bodies in a patient, the vertebral implant comprising:

a spacer member including opposing first and second ends;

a first end member including a first receptacle to receive the first end of the spacer and an opposing first contact surface configured to contact against one of the vertebral bodies;

a second end member including a first surface, an opposing second surface, and an intermediate wall that extends between the first and second surfaces, the second surface configured to contact against another of the vertebral bodies; and a second receptacle that extends into the first surface and the intermediate wall of the second end member, the second receptacle including a bottom wall opposite from the first surface that defines a depth of the second receptacle and receives the second end of the spacer, and a ledge positioned between the bottom wall and the first surface;

the implant including a longitudinal axis that extends through the first and second end members and the spacer member with the ledge being uncovered in a direction directly towards the first end member.

9. The vertebral implant of claim 8 wherein the bottom wall and the ledge are parallel.

* * * * *